United States Patent [19]

United States Patent [19]
Tomcufcik et al.

[11] Patent Number: 4,582,833
[45] Date of Patent: Apr. 15, 1986

[54] 2-(SUBSTITUTED-1-PIPERAZINYL)[1,2,4]-TRIAZOLO[1,5-A]PYRIMIDINES

[75] Inventors: Andrew S. Tomcufcik, Old Tappan, N.J.; Walter E. Meyer, Suffern; John P. Dusza, Nanuet, both of N.Y.

[73] Assignee: American Cyanamid Company, Stamford, Conn.

[21] Appl. No.: 600,937

[22] Filed: Apr. 16, 1984

[51] Int. Cl.$^4$ ..................... A61K 31/41; C07D 487/04
[52] U.S. Cl. .................................... 514/258; 544/263; 544/366
[58] Field of Search ....................... 544/263; 424/251; 514/258

[56] References Cited

U.S. PATENT DOCUMENTS 4,036,840 7/1977 O'Brien .............................. 424/251
4,497,814 2/1985 Witkowski .......................... 514/258

OTHER PUBLICATIONS

Okabe et al., J. Heterocyclic Chemistry, 20, p. 735 (1983).
Miller & Rose, J. Chemical Society, 3357 (1965).

Primary Examiner—Donald G. Daus
Assistant Examiner—Robert Benson
Attorney, Agent, or Firm—E. A. Conroy, Jr.

[57] ABSTRACT

This disclosure describes novel 2-(4-substituted-1-piperazinyl)[1,2,4]triazolo[1,5-a]pyrimidines useful as hypotensive agents.

19 Claims, No Drawings

2-(SUBSTITUTED-1-PIPERAZINYL)[1,2,4]-TRIAZOLO[1,5-A]PYRIMIDINES

BRIEF SUMMARY OF THE INVENTION

This invention relates to new organic compounds and, more particularly, is concerned with novel 2-(4-substituted-1-piperazinyl)[1,2,4]triazolo[1,5-a]pyrimidines which have hypotensive activity. The compounds of the present invention may be represented by the following structural formula:

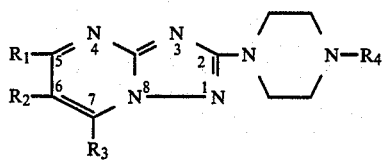
(I)

wherein $R_1$ is hydrogen, n-propyl or trifluoromethyl; $R_2$ is hydrogen or bromo; $R_3$ is selected from the group consisting of hydrogen, n-propyl, 3-chlorophenyl, 2,5-dichlorophenyl, 3-trifluoromethylphenyl, 2-furyl, 3-pyridyl, 4-pyridyl, diphenylmethyl and moieties of the formulae:

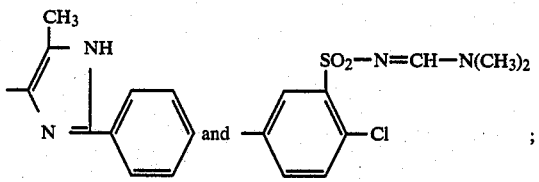

and $R_4$ is selected from the group consisting of hydrogen, methyl, formyl, carbothoxy, carbobenzyloxy, benzyl, 3-chlorobenzyl, 3,4-dichlorobenzyl, β-phenethyl, furfuryl, 4-pyridyl, cyclopentyl, N-iso-propylaminocarbonylmethyl, 3-cyanopropyl, 3-(4-fluorobenzoyl)propyl, 2-propenyl, 2-benzoylethyl, 3-phenyl-2-propenyl, 2-phenoxyethyl, 3-phenoxypropyl, 4-phenoxybutyl, 2-(4-bromophenoxy)ethyl, 2-hydroxy-3-phenoxypropyl and a moiety of the formula:

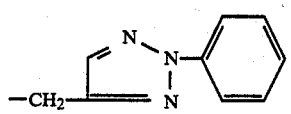

and the pharmacologically acceptable acid-addition salts thereof.

Also included within the purview of the present invention are compounds of the formula:

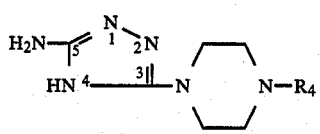
(II)

wherein $R_4$ is selected from the group consisting of methyl, formyl, carboethoxy, N-iso-propylaminocarbonylmethyl, benzyl, 3-chlorobenzyl, 3,4-dichlorobenzyl, β-phenethyl, 2-propenyl, 3-phenyl-2-propenyl, 2-phenoxyethyl, 3-phenoxypropyl, 4-phenoxybutyl, 2-(4-bromophenoxy)ethyl, 4-pyridyl, furfuryl, cyclopentyl and a moiety of the formula:

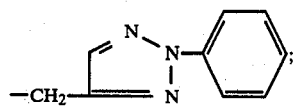

said compounds being useful as intermediates for the preparation of the novel 2-(4-substituted-1-piperazinyl)[1,2,4]triazolo[1,5-a]pyrimidine compounds of the present invention encompassed by structural formula (I).

In general formula (II) the hydrogen is placed on the nitrogen in the 4-position as a matter of convenience. It is obvious that the hydrogen could also be found on the nitrogen in the 1-position or 2-position, as follows:

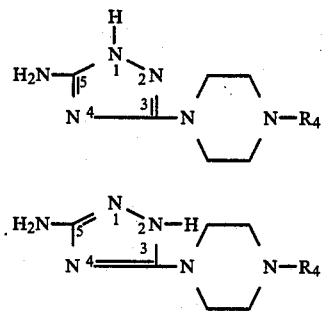

All three tautomeric structures are included within the scope of the present invention. The invention also includes novel compositions of matter containing the above-defined compounds of formula (I) which are useful as hypotensive agents and the method of treating hypertension in mammals therewith.

DETAILED DESCRIPTION OF THE INVENTION

The novel compounds of the present invention are, in general, obtainable as colorless, yellow or tan crystalline materials having characteristic melting points and absorption spectra. They are appreciably soluble in many organic solvents such as lower alkanols, chloroform, dichloromethane, tetrahydrofuran, acetone, N,N-dimethylformamide, and the like, but are generally insoluble in water. These compounds are organic bases and thus are capable of forming acid-addition salts with a variety of organic and inorganic salt-forming reagents. Thus, acid-addition salts, formed by admixture of the organic free base with an equivalent of an acid, suitably in a neutral solvent, are formed with such acids as sulfuric, phosphoric, hydrochloric, hydrobromic, sulfamic, citric, maleic, fumaric, tartaric, acetic, benzoic, gluconic, ascorbic, and related acids. The acid-addition salts of the novel compounds of the present invention are, in general, crystalline solids relatively soluble in water, methanol and ethanol but relatively insoluble in non-polar organic solvents such as diethyl ether, benzene, toluene and the like. For purposes of this invention the free bases are equivalent to their non-toxic acid-addition salts.

The novel compounds of the present invention where $R_1$ and $R_2$ are both hydrogen in structural formula (I), may be readily prepared as set forth in the following reaction scheme (A).

SCHEME A

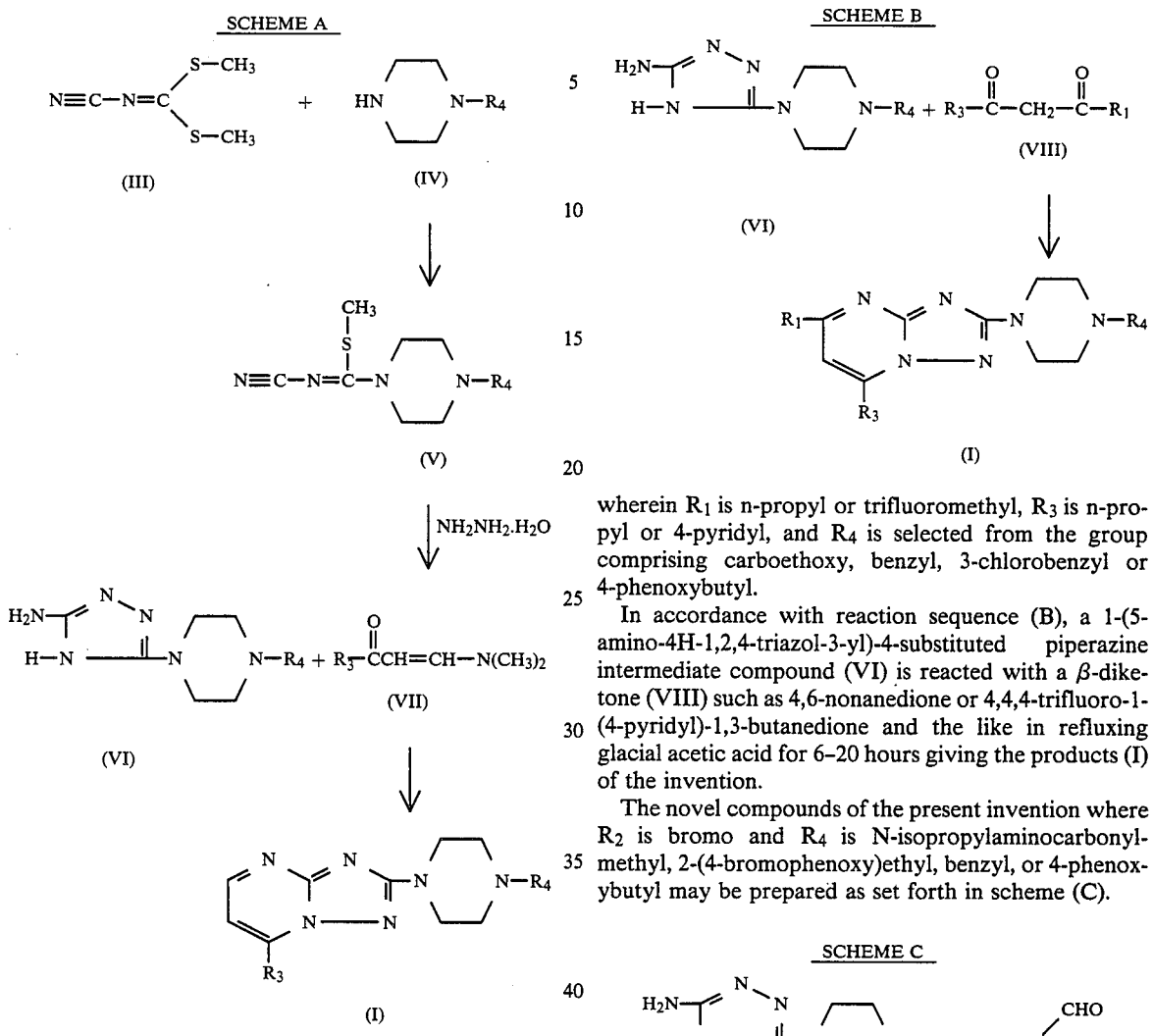

wherein $R_3$ is as hereinabove described with the exclusion of n-propyl, and $R_4$ is as hereinabove described with the exclusion of N-isopropylaminocarbonylmethyl.

In accordance with the above reaction sequence, dimethyl cyanodithioiminocarbonate (III) and a piperazine (IV) where $R_4$ is as hereinabove described, are refluxed in acetonitrile, ethanol or a similar solvent for 4–18 hours, giving a solution of N-cyano-4-substituted-1-piperazinecarboximidothioic acid, methyl ester (V), which is then refluxed with hydrazine hydrate in the solvent giving the 1-(5-amino-4H-1,2,4-triazol-3-yl)-4-substituted-piperazine intermediate compounds (VI). The intermediate (VI) is reacted with a 3-dimethylamino-1-(aryl, substituted aryl or heteroaryl)-2-propen-1-one (VII) in refluxing glacial acetic acid for one to 20 hours to provide the products (I) of the invention.

The novel compounds of the present invention where $R_1$ may be other than hydrogen as hereinabove defined may be prepared as set forth in the following reaction scheme (B).

SCHEME B

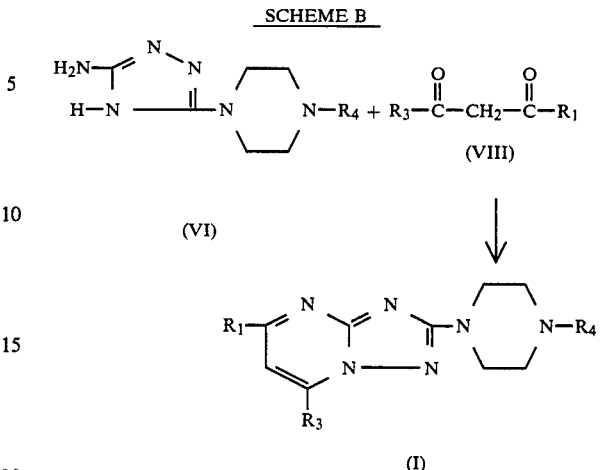

wherein $R_1$ is n-propyl or trifluoromethyl, $R_3$ is n-propyl or 4-pyridyl, and $R_4$ is selected from the group comprising carboethoxy, benzyl, 3-chlorobenzyl or 4-phenoxybutyl.

In accordance with reaction sequence (B), a 1-(5-amino-4H-1,2,4-triazol-3-yl)-4-substituted piperazine intermediate compound (VI) is reacted with a β-diketone (VIII) such as 4,6-nonanedione or 4,4,4-trifluoro-1-(4-pyridyl)-1,3-butanedione and the like in refluxing glacial acetic acid for 6–20 hours giving the products (I) of the invention.

The novel compounds of the present invention where $R_2$ is bromo and $R_4$ is N-isopropylaminocarbonylmethyl, 2-(4-bromophenoxy)ethyl, benzyl, or 4-phenoxybutyl may be prepared as set forth in scheme (C).

SCHEME C

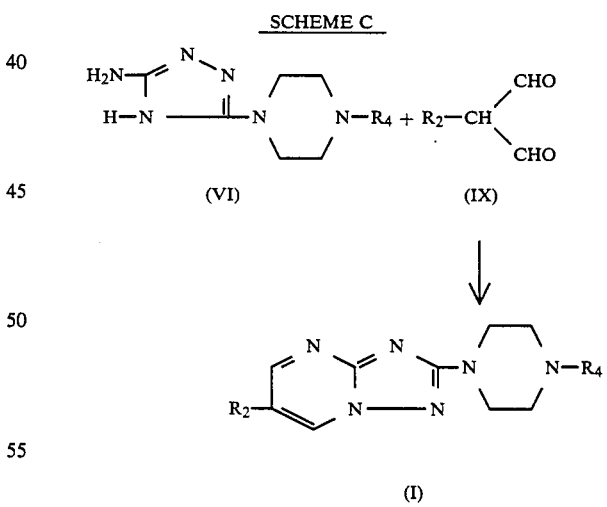

In accordance with reaction sequence (C), a 1-(5-amino-4H-1,2,4-triazol-3-yl)-4-substituted piperazine intermediate (VI) is reacted with a malonaldehyde (IX) such as bromomalonaldehyde and the like in refluxing ethanol for 2–20 hours giving the products (I) of the invention.

The intermediate 1-(5-amino-4H-1,2,4-triazol-3-yl)-4-substituted-piperazine compounds (IV) are, in general, prepared as described in U.S. Pat. No. 4,421,753. The 3-dimethylamino-1-(aryl, substituted aryl or heteroaryl)-2-propen-1-one reactants (VII) are prepared as described in U.S. Pat. No. 4,281,000.

The novel compounds of the present invention are active hypotensive agents and were tested for hypotensive activity by the method of P. S. Chan and D. Poorvin, *Clinical and Experimental Hypertension*, 1 (6), 817–380 (1979). Male, 16 week old, spontaneously hypertensive rats of the Okamoto strain, from Taconic Farms, Germantown, N.Y., having an average mean arterial blood pressure of 170±1.5 mm of mercury are used in the test. One to 3 rats are used per test compound. A rat is dosed by gavage with a test compound suspended in 2% pre-boiled starch, at a concentration of 50 mg/ml, at a dose of 100 mg/kg of body weight or less, with 0.9% sodium chloride loading at a dose of 25 ml/kg of body weight. A second identical dose of the test compound, without sodium chloride loading, is given 24 hours later. At 28 hours after the initial dose the mean arterial blood pressure is measured by the method of Chan and Poorvin vide supra. The procedure is repeated in a second and third rat when necessary.

The results of this test on representative compounds of the present invention, which were obtained using one or two rats, at a dose of 100 mg/kg of body weight, appear in Table I below.

TABLE I

| Compound | Mean Arterial Blood Pressure (mm of mercury) |
|---|---|
| 2-(4-Benzyl-1-piperazinyl)-7-(3-pyridyl)[1,2,4]triazolo[1,5-a]pyrimidine | 124 |
| | 115 |
| 2-(4-Benzyl-1-piperazinyl)-7-(α,α,α-trifluoro-m-tolyl)[1,2,4]triazolo[1,5-a]pyrimidine | 126 |
| | 118 |
| 2-(4-Benzyl-1-piperazinyl)-7-(2,5-dichlorophenyl)[1,2,4]triazolo[1,5-a]pyrimidine | 129 |
| | 121 |
| 2-(4-Benzyl-1-piperazinyl)-7-(2-furyl)-[1,2,4]triazolo[1,5-a]pyrimidine | 123 |
| | 115 |
| 2-(4-Benzyl-1-piperazinyl)-7-(4-pyridyl)[1,2,4]triazolo[1,5-a]pyrimidine | 112 |
| 7-(4-Pyridyl)-2-[4-(4-pyridylmethyl)-1-piperazinyl][1,2,4]triazolo[1,5-a]pyrimidine | 89 |
| 4-(5,7-Dipropyl[1,2,4]triazolo[1,5-a]pyrimidin-2-yl)-1-piperazinecarboxylic acid, ethyl ester | 108 |
| | 118 |
| 2-(4-Benzyl-1-piperazinyl)-5,7-dipropyl[1,2,4]triazolo[1,5-a]pyrimidine | 121 |
| | 108 |
| 2-(4-Phenethyl-1-piperazinyl)-7-(4-pyridyl)[1,2,4]triazolo[1,5-a]pyrimidine | 90 |
| 7-Diphenylmethyl-2-(4-phenethyl-1-piperazinyl)[1,2,4]triazolo[1,5-a]pyrimidine | 118 |
| | 108 |
| 2-(4-Methyl-1-piperazinyl)-7-(4-pyridyl)[1,2,4]triazolo[1,5-a]pyrimidine | 123 |
| | 136 |
| 2-(4-Furfuryl-1-piperazinyl)-7-(4-pyridyl)[1,2,4]triazolo[1,5-a]pyrimidine | 123 |
| | 121 |
| 2-(4-Cyclopentyl-1-piperazinyl)-7-(3-pyridyl)[1,2,4]triazolo[1,5-a]pyrimidine | 110 |
| 2-(4-Cyclopentyl-1-piperazinyl)-7-(4-pyridyl)[1,2,4]triazolo[1,5-a]pyrimidine | 96 |
| 4-[7-(4-Pyridyl)[1,2,4]triazolo[1,5-a]pyrimidin-2-yl]-1-piperazinecarboxaldehyde | 123 |
| | 112 |
| 2-(1-Piperazinyl)-7-(4-pyridyl)[1,2,4]triazolo[1,5-a]pyrimidine | 103 |
| | 94 |
| 2-[4-m-Chlorobenzyl-1-piperazinyl]-7-(4-pyridyl)[1,2,4]triazolo[1,5-a]pyrimidine | 120 |
| | 109 |
| 2-[4-(3,4-Dichlorophenyl)methyl]-1-piperazinyl]-7-(4-pyridyl)[1,2,4]triazolo[1,5-a]pyrimidine | 99 |
| | 109 |
| 2-[4-(2-Propenyl)-1-piperazinyl]-7-(4-pyridinyl)[1,2,4]triazolo[1,5-a]pyrimidine | 90 |
| | 118 |
| 2-[4-[(3-Chlorophenyl)methyl]-1-piperazinyl]-5,7-dipropyl[1,2,4]triazolo[1,5-a]pyrimidine, monohydrochloride | 130 |
| | 119 |
| 2-(1-Piperazinyl)-7-(3-pyridinyl)-[1,2,4]triazolo[1,5-a]pyrimidine | 114 |
| 2-[4-[2-(4-Bromophenoxy)ethyl]-1-piperazinyl]-7-[4-pyridinyl][1,2,4]triazolo[1,5-a]pyrimidine | 111 |
| | 126 |
| 6-Bromo-2-[4-(4-phenoxybutyl)-1-piperazinyl][1,2,4]triazolo[1,5-a]pyrimidine | 140 |
| | 123 |
| 4-(6-Bromo[1,2,4]triazolo[1,5-a]pyrimidin-2-yl)-N—(1-methylethyl)-1-piperazineacetamide | 127 |
| | 111 |
| 7-(3-Chlorophenyl)-2-[4-(3,4-dichlorophenyl)methyl-1-piperazinyl][1,2,4]triazolo[1,5-a]pyrimidine, hydrochloride (3:2) | 135 |
| | 118 |
| 1-Phenyl-2-[4-[7-(4-pyridinyl)[1,2,4]triazolo[1,5-a]pyrimidin-2-yl]-1-piperazinyl]-1-propanone | 121 |
| | 142 |
| N—(1-Methylethyl)-4-[7-(4-pyridinyl)-[1,2,4]triazolo[1,5-a]pyrimidin-2-yl]-1-piperazineacetamide | 127 |
| | 117 |
| 2-[4-(3-Phenoxypropyl)-1-piperazinyl]-7-(4-pyridinyl)[1,2,4]triazolo[1,5-a]pyrimidine | 116 |
| | 125 |
| 4-[7-(4-Pyridinyl)[1,2,4]triazolo-[1,5-a]pyrimidin-2-yl]-1-piperazinebutanenitrile | 126 |
| | 111 |
| 1-(4-Fluorophenyl)-4-[4-[7-(4-pyridinyl)[1,2,4]triazolo[1,5-a]pyrimidin-2-yl]-1-piperazinyl]-1-butanone | 120 |
| | 90 |
| 2-[4-(4-Phenoxybutyl)-1-piperazinyl]-7-(4-pyridinyl)[1,2,4]triazolo[1,5-a]pyrimidine | 125 |
| | 119 |
| 2-[4-[(2-Phenyl-2H—1,2,3-triazol-4-yl)-methyl]-1-piperazinyl]-7-(4-pyridinyl)-[1,2,4]triazolo[1,5-a]pyrimidine | 118 |
| | 126 |
| 6-Bromo-2-[4-[2-(4-bromophenoxy)ethyl]-1-piperazinyl][1,2,4]triazolo[1,5-a]pyrimidine | 123 |
| | 121 |
| 2-[4-(Phenylmethyl)-1-piperazinyl]-7-(4-pyridinyl)-5-(trifluoromethyl)-[1,2,4]triazolo[1,5-a]pyrimidine | 114 |
| | 111 |
| α-(Phenoxymethyl)-4-[7-(4-pyridinyl)-[1,2,4]triazolo[1,5-a]pyrimidin-2-yl]-1-piperazineethanol | 129 |
| | 120 |
| 2-[4-(2-Phenoxyethyl)-1-piperazinyl]-7-(4-pyridinyl)[1,2,4]triazolo[1,5-a]pyrimidine | 95 |
| | 92 |
| 2-[4-(4-Phenoxybutyl)-1-piperazinyl]-5,7-dipropyl[1,2,4]triazolo[1,5-a]pyrimidine, monohydrochloride | 113 |
| | 112 |
| 7-(5-Methyl-2-phenyl-1H—imidazo-4-yl)-2-[4-(phenylmethyl)-1-piperazinyl]-[1,2,4]triazolo[1,5-a]pyrimidine | 124 |
| | 125 |
| N'—[[2-Chloro-5-[2-[4-(phenylmethyl)-1-piperazinyl]triazolo[1,5-a]pyrimidin-7-yl]phenyl]sulfonyl]-N—N—dimethyl methanimidamide | 125 |
| | 128 |
| 6-Bromo-2-[4-(phenylmethyl)-1-piperazinyl][1,2,4]triazolo[1,5-a]pyrimidine | 120 |
| | 123 |
| 2-[4-(3-Phenyl-2-propenyl)-1-piperazinyl]-7-(4-pyridinyl)[1,2,4]triazolo-[1,5-a]pyrimidine | 148 |
| | 130 |

The active compounds of the present invention are effective hypotensive agents in warm-blooded animals when administered in amounts ranging from about 5 mg to about 200 mg per kilogram of body weight per day. A preferred dosage regimen for optimum results would be from about 5 mg to about 50 mg per kilogram of body weight per day, and such dosage units are employed that a total of from about 350 mg to about 3.5 g of the active compound for a subject of about 70 kg of body weight are administered in a 24 hour period. This dosage regimen may be adjusted to provide the optimum therapeutic response. For example, several divided doses may be proportionally reduced as indicated by the exigencies of the therapeutic situation. A decided practical advantage is that these active compounds may be administered in any convenient manner such as by the oral, intravenous, intramuscular or subcutaneous routes.

The active compounds may be orally administered, for example, with an inert diluent or with an assimilable edible carrier, or they may be enclosed in hard or soft shell gelatin capsules, or they may be compressed into tablets, or they may be incorporated directly with the food of the diet. For oral therapeutic administration, these active compounds may be incoporated with excipients and used in the form of ingestible tablets, buccal tablets, troches, capsules, elixirs, suspensions, syrups, wafers and the like. Such compositions and preparations should contain at least 0.1% of active compound. The percentage of the compositions and preparations may, of course, be varied and may conveniently be between about 2% to about 60% of the weight of the unit. The amount of active compound in such therapeutically useful compositions is such that a suitable dosage will be obtained. Preferred compositions or preparations according to the present invention are prepared so that an oral dosage unit form contains between about 5 and 200 mg of active compound.

The tablets, troches, pills, capsules and the like may also contain the following: A binder such as gum tragacanth, acacia, corn starch or gelatin; excipients such as dicalcium phosphate; a disintegrating agent such as corn starch, potato starch, alginic acid and the like; a lubricant such as magnesium stearate; and a sweetening agent such as sucrose, lactose or saccharin may be added or a flavoring agent such as peppermint, oil of wintergreen or cherry flavoring. When the dosage unit form is a capsule, it may contain, in addition to materials of the above type, a liquid carrier. Various other materials may be present as coatings or to otherwise modify the physical form of the dosage unit. For instance, tablets, pills or capsules may be coated with shellac, sugar or both. A syrup or elixir may contain the active compound, sucrose as a sweetening agent, methyl and propylparabens as preservatives, a dye and flavoring such as cherry or orange flavor. Of course, any material used in preparing any dosage unit form should be pharmaceutically pure and substantially non-toxic in the amounts used. In addition, these active compounds may be incorporated into sustained-release preparations and formulations.

These active compounds may also be administered parenterally or intraperitoneally. Solutions or suspensions of these active compounds as a free base or pharmacologically acceptable salt can be prepared in water suitably mixed with a surfactant such as hydroxypropylcellulose. Dispersions can also be prepared in glycerol, liquid polyethylene glycols, and mixtures thereof in oils. Under ordinary conditions of storage and use, these preparations contain a preservative to prevent the growth of microorganisms.

The pharmaceutical forms suitable for injectable use include sterile aqueous solutions or dispersions and sterile powders for the extemporaneous preparation of sterile injectable solutions or dispersions. In all cases, the form must be sterile and must be fluid to the extent that easy syringability exists. It must be stable under the conditions of manufacture and storage and must be prepserved against the contaminating action of microorganisms such as bacteria and fungi. The carrier can be a solvent or dispersion medium containing, for example, water, ethanol, polyol (e.g. glycerol, propylene glycol and liquid polyethylene glycol), suitable mixtures thereof, and vegetable oils.

The invention will be described in greater detail in conjunction with the following specific examples.

EXAMPLE 1

1-(5-Amino-4H-1,2,4-triazol-3-yl)-4-(4-pyridylmethyl)-piperazine

A mixture of 37.2 g of 4-picolyl chloride hydrochloride, 39.6 g of ethyl-1-piperazine carboxylate, 400 ml of 2-propanol and 55.0 ml of 10N sodium hydroxide was refluxed for 18 hours. The reaction mixture was evaporated in vacuo to give a dark red syrup. The syrup was distilled collecting 26.0 g of 4-(4-pyridylmethyl)-1-piperazinecarboxylic acid, ethyl ester as a colorless syrup, bp 157°–160° C./0.02 mm of mercury.

A 25.0 g portion of the preceding product was refluxed for 16 hours in 100 ml of 47–49% hydrobromic acid. The solution was evaporated near dryness with crystal formation. The mixture was cooled and filtered and the collected solid was washed with ethanol and gave 27.0 g of 1-(4-pyridylmethyl)piperazine trihydrobromide, mp 268°–269° C. (dec.).

A 26.0 g portion of the preceding material in water was adjusted to pH 7.0 with 10N sodium hydroxide, and extracted with two 50 ml portions of chloroform. The combined chloroform extract was dried over magnesium sulfate, evaporated in vacuo and gave 11.3 g of a colorless syrup. The syrup was distilled, and the fraction, bp 166°–168° C./15 mm, was collected and gave 9.4 g of 1-(4-pyridylmethyl)piperazine as a colorless liquid.

A 17.7 g (0.1 mole) amount of 1-(4-pyridylmethyl)piperazine (prepared as described above) was dissolved in 25 ml of ethanol and then added dropwise over 30 minutes to a stirred solution of 14.6 g (0.1 mole) of dimethyl cyanodithioiminocarbonate in 125 ml of ethanol. The mixture was refluxed for 20 hours, the evolved gas being led into a sodium hypochlorite trap, for the first 3 hours. Then 6.0 ml (0.12 mole) of hydrazine hydrate was added into the refluxing reaction mixture through the condenser and the mixture was refluxed for 6 hours longer. The mixture was evaporated to a solid residue which was recrystallized with ether and gave 25.8 g of the product of the Example as pale yellow crystals, mp 191°–193° C.

EXAMPLE 2

4-(5-Amino-4H-1,2,4-triazol-3-yl)-1-piperazinecarboxylic acid, ethyl ester

A combined mixture of 14.6 g (0.1 mole) of dimethyl cyanodithioiminocarbonate in 200 ml of ethanol and 15.8 g (0.1 mole) of ethyl N-piperazinocarboxylate in 30 ml of ethanol was refluxed for 7 hours, the evolved gas being swept into a sodium hypochlorate trap with air. The mixture was evaporated to a syrup and crystallized from 2-propanol:hexane with cooling and gave 22.2 g of 4-carboxy-N-cyano-1-piperazinecarboximidothioic acid 4-ethyl methyl ester, mp 67°–69° C.

To a suspension of 20.5 g (0.080 moles) of the preceding product in 100 ml of ethanol was added 4.5 ml (0.088 moles) of hydrazine hydrate. The mixture was refluxed for 18 hours. The reaction mixture was evaporated to a syrup, and crystallized from ethanol and gave 15.8 g of the desired product as colorless crystals, mp 196°–198° C.

EXAMPLE 3

4-(5-Amino-4H-1,2,4-triazol-3-yl)-1-piperazinecarboxaldehyde

A mixture of 11.4 g (0.1 mole) of piperazinecarboxaldehyde, 14.6 g (0.1 mole) of dimethyl cyanodithioiminocarbonate and 150 ml of acetonitrile was heated at reflux for 18 hours, the evolved gas being led into a sodium hypochlorite trap. The reaction mixture was cooled and filtered to remove a small amount of colorless solid. The filter was washed with acetonitrile, the wash being added to the filtrate. Then 5.5 ml (0.11 mole) of hydrazine hydrate was added to the filtrate and the mixture was refluxed for 4 hours, again with a sodium hypochlorite trap installed. Crystals appeared during reflux. The mixture was cooled and filtered. The material was washed with acetonitrile and gave 17.8 g of the product of the Example, mp 150°–151° C. (dec.).

EXAMPLE 4

4-(5-Amino-4H-1,2,4-triazol-3-yl)-1-piperazinecarboxylic acid, benzyl ester

As for Example 3, a mixture of 66.0 g (0.3 moles) of benzyl N-piperazinecarboxylate and 43.8 g (0.3 moles) of dimethyl cyanodithioiminocarbonate in 300 ml of acetonitrile was refluxed for 16 hours. After cooling, filtration and washing, 16.0 ml (0.32 moles) of hydrazine hydrate was added to the filtrate and the mixture was refluxed for 4 hours. Cooling, filtration, and washing with cold acetonitrile, then hexane gave 74.7 g of the desired product as colorless crystals, mp 157°–159° C.

EXAMPLE 5

1-(5-Amino-4H-1,2,4-triazol-3-yl)-4-(3,4-dichlorobenzyl)piperazine

A mixture of 39.0 g (0.2 moles) of 3,4-dichlorobenzyl chloride, 31.6 g (0.2 moles) of ethyl N-piperazinocarboxylate, 22.0 g (0.21 moles) of anhydrous sodium carbonate and 200 ml of xylene was refluxed for 3 hours using a Dean-Stark trap. Then the mixture was stirred at room temperature for 16 hours, filtered and washed with xylene. The filtrate was evaporated in vacuo to give a syrup. A 750 ml amount of 4N potassium hydroxide in 95% ethanol was added to the syrup and the mixture was refluxed for 18 hours. The reaction mixture was evaporated to a paste and 250 ml of water was added. The solution was extracted twice with 250 ml of chloroform. The extracts were combined, dried over magnesium sulfate and filtered. The filtrate was evaporated in vacuo and gave a syrup. The syrup was distilled, bp 132°–135° C./0.05 mm of mercury and gave 9.3 g of 1-(3,4-dichlorobenzyl)piperazine as a colorless liquid.

In the manner of Example 3, a mixture of 7.3 g of the preceding piperazine and 4.4 g of dimethyl cyanodithioiminocarbonate in 100 ml of acetonitrile was refluxed for 3 hours. After cooling, filtration and washing, 1.6 ml of hydrazine hydrate was added to the filtrate and the mixture was refluxed for 3 hours. Cooling in an ice bath, filtration and washing with ether gave 7.5 g of product. The material was recrystallized from ethanol and gave 4.3 g of the product of the Example as colorless crystals, mp 163°–164° C.

EXAMPLE 6

1-(5-Amino-4H-1,2,4-triazol-3-yl)-4-[2-(4-bromophenoxy)ethyl]piperazine

A mixture of 56.0 g (0.2 moles) of 2-bromoethyl p-bromophenyl ether and 45.6 g (0.4 moles) of 1-formylpiperazine in 500 ml of 2-propanol was heated at reflux for 18 hours. The mixture was cooled and filtered. The filter was washed with 2-propanol and the filtrate was evaporated to an oil in vacuo. Water was added and the oil was extracted three times with about 200 ml of chloroform. The extracts were combined, dried over magnesium sulfate and filtered. The filtrate was evaporated to an oil to which 250 ml of 5N sodium hydroxide was added. The mixture was refluxed for 18 hours, cooled and extracted three times with about 200 ml of chloroform. The extracts were combined, dried over magnesium sulfate and evaporated to an oil. The oil was distilled, bp 125°–128° C./0.05 mm of mercury, and gave 40 g of 1-[2-(4-bromophenoxy)ethyl]-piperazine as a yellowing oil.

The procedure of Example 3 was followed substituting 28.5 g of 1-[2-(4-bromophenoxy)ethyl]piperazine for piperazinecarboxaldehyde while using 300 ml of acetonitrile. Continuing the procedure, the reflux period with hydrazine hydrate was reduced from 4 hours to one hour. The reaction mixture was evaporated in vacuo giving a syrup which crystallized on standing. The material was recrystallized from ethanol after treatment with activated charcoal and gave 18.9 g of the desired product as colorless crystals, mp 166°–167° C.

EXAMPLE 7

5-[4-(4-Phenoxybutyl)-1-piperazinyl]-4H-1,2,4-triazol-3-amine, dihydrochloride

The procedure of Example 6 was repeated substituting 45.8 g (0.2 moles) of 4-phenoxybutyl bromide for 2-bromoethyl p-bromophenyl ether and continuing to obtain an amber oil which was distilled, bp 153°–156° C./0.05 mm and gave 33.4 g of 1-(4-phenoxybutyl)piperazine as a colorless liquid which crystallized on standing, mp 35°–36° C.

The procedure of Example 6 was continued substituting 23.4 g (0.1 mole) of 1-(4-phenoxybutyl)piperazine for 1-[2-(4-bromophenoxy)ethyl]piperazine and using a total of 350 ml of acetonitrile. Continuing after reflux with hydrazine hydrate the reaction mixture was evaporated in vacuo and gave 30.8 g of a pink syrup.

An 18.0 g amount of the syrup was dissolved in 100 ml of ethanol then 50 ml of 3.7N ethanolic hydrochloric acid was added and the mixture was cooled at 5° C. The crystallized product was collected by filtration, washed with ethanol:ether then ether and gave 18.2 g of the product of the example as colorless crystals, mp 245°–246° C. (dec.).

EXAMPLE 8

4-(5-Amino-4H-1,2,4-triazol-3-yl)-N-(1-methylethyl)-1-piperazineacetamide

The procedure of Example 6 was repeated substituting 18.5 g (0.1 mole) of N-isopropyl-1-piperazineacetamide for 1-[2-(4-bromophenoxy)ethyl]piperazine and continuing through the hydrazine hydrate reflux. Then cooling the reaction mixture in an ice bath to crystallize the product which was collected by filtration and washed with ether and gave 18.6 g of the desired product as colorless crystals, mp 225°–226° C.

EXAMPLE 9

1-(5-Amino-4H-1,2,4-triazol-3-yl)-4-(2-phenoxyethyl)-piperazine

The procedure of Example 6 was repeated, substituting 57.0 g (0.27 moles) of 2-bromoethyl phenyl ether for 2-bromoethyl p-bromophenyl ether, using 61.6 g (0.54 moles) of 1-formylpiperazine in 300 ml of 2-propanol and refluxing the mixture for 8 hours. Evaporation of the final dried chloroform extracts gave 35 g of 1-[2-phenoxyethyl]piperazine as an oil.

In the manner of Example 3 a mixture of 10.3 g (0.05 moles) of 1-[2-phenoxyethyl]piperazine and 7.3 g (0.05 moles) of dimethyl cyanodithioiminocarbonate in 250 ml of acetonitrile was refluxed for 3 hours. After cooling, 2.8 ml (0.056 moles) of hydrazine hydrate was added and the mixture was refluxed for 45 minutes. The mixture was cooled, filtered through diatomaceous earth and the filtrate was evaporated to a paste. The product was crystallized from ethanol/ether/hexane, collected and washed with ether and gave 5.3 g of colorless crystals, mp 131°–133° C.

EXAMPLE 10

1-(5-Amino-4H-1,2,4-triazol-3-yl)-4-benzylpiperazine

A mixture of 21.2 g of dimethyl cyanodithioiminocarbonate and 35.3 g of 1-benzylpiperazine in 400 ml of absolute ethanol was heated at the reflux temperature for 6 hours. The resulting solution was evaporated in vacuo. Water was added to the residue with stirring and the mixture was filtered to collect 46.3 g of 4-benzyl-N-cyano-1-piperazinecarboximidothioic acid methyl ester was colorless prisms, mp 72°–74° C.

A 27.44 g amount of the preceding product was reacted with 5.50 g of hydrazine hydrate in 100 ml of absolute ethanol by refluxing for 6 hours. The reaction mixture was cooled, activated charcoal was added, then the mixture was filtered through diatomaceous earth and the filtrate was evaporated in vacuo. Water was added to the residue with stirring and the mixture was filtered to collect 23.8 g of the product of the Example as colorless crystals, mp 160°–161° C.

EXAMPLE 11

4-Dimethylamino-1,1-diphenyl-3-buten-2-one

A mixture of 21.0 g of 1,1-diphenylacetone and 40 ml of N,N-dimethylformamide dimethyl acetal in a 300 ml round bottom flask was heated in an oil bath at 120° C. for 8 hours with ethanol being distilled over. The reaction mixture was cooled and evaporated in vacuo to give an oil. The oil was boiled up in 50 ml of ether then cooled at −10° C. and gave a heavy precipitate. The precipitate was collected, washed with ether, then air dried and gave 21.5 g of crude product. A 5.0 g portion was recrystallized from 50 ml of 2-propanol, then cooled at room temperature. The material was collected and dried at 60° C. and gave 1.7 g of the desired product, mp 93°–94° C.

EXAMPLE 12

2-(4-Benzyl-1-piperazinyl)-7-(3-pyridyl)[1,2,4]-triazolo[1,5-a]pyrimidine

A mixture of 2.58 g of (1-(5-amino-4H-1,2,4-triazol-3-yl)-4-benzylpiperazine and 1.76 g of 3-dimethylamino-1-(3-pyridyl)-2-propen-1-one (U.S. Pat. No. 4,281,000, Example 1) in 35 ml of glacial acetic acid was refluxed for 12 hours. The solution was taken to dryness in vacuo. The residue was partitioned between saturated sodium bicarbonate and dichloromethane (1:2). The dichloromethane layer was separated, dried over anhydrous sodium sulfate and filtered through a short column of magnesium silicate. The effluent was refluxed on a steam bath with the gradual addition of hexane until turbidity was noted. After cooling the precipitate was collected by filtration. The solid was recrystallized from dichloromethane/hexane and gave 2.20 g of the desired product as pale yellow crystals, mp 149°–150° C.

EXAMPLES 13–37

Additional examples of 2-(4-substituted-1-piperazinyl)-7-substituted[1,2,4]triazolo[1,5-a]pyrimidines which are listed in Table II were prepared in the manner described in Example 12, by reacting equimolar amounts of a 1-(5-amino-4H-1,2,4-triazol-3-yl)-4-substituted piperazine (hereinabove disclosed or prepared as described in U.S. Pat. No. 4,421,753) and a 3-dimethylamino-1-(aryl, substituted aryl, diaryl or heteroaryl)-2-propen-1-one (described herein, or disclosed in U.S. Pat. No. 4,281,000 and prepared by the procedure described therein).

TABLE II 2-(4-Substituted-1-piperazinyl)-7-substituted[1,2,4]triazolo[1,5-a]pyrimidines

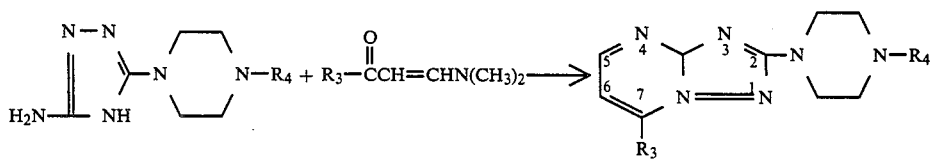

| Ex. | Compound | R$_3$ | R$_4$ | Description | MP °C. |
|---|---|---|---|---|---|
| 13 | 2-(4-Benzyl-1-piperazinyl)-7-(α,α,α-trifluoro-m-tolyl)[1,2,4]triazolo[1,5-a]pyrimidine | 3-(F$_3$C)-C$_6$H$_4$- | —CH$_2$—C$_6$H$_5$ | very pale yellow crystals | 124–126 |

TABLE II-continued
2-(4-Substituted-1-piperazinyl)-7-substituted[1,2,4]triazolo[1,5-a]pyrimidines

| Ex. | Compound | R₃ | R₄ | Description | MP °C. |
|---|---|---|---|---|---|
| 14 | 2-(4-Benzyl-1-piperazinyl)-7-(2,5-dichlorophenyl)-[1,2,4]triazolo[1,5-a]pyrimidine | 2,5-dichlorophenyl | —CH₂—phenyl | pale yellow crystals | 137–138 |
| 15 | 2-(4-Benzyl-1-piperazinyl)-7-(2-furyl)[1,2,4]triazolo[1,5-a]pyrimidine | 2-furyl | —CH₂—phenyl | pale yellow needles | 153–154 |
| 16 | 2-(4-Benzyl-1-piperazinyl)-7-(4-pyridyl)[1,2,4]triazolo[1,5-a]pyrimidine | 4-pyridyl | —CH₂—phenyl | pale yellow crystals | 178–180 |
| 17 | 7-(4-Pyridyl)-2-[4-(4-pyridylmethyl)-1-piperazinyl][1,2,4]triazolo[1,5-a]pyrimidine | 4-pyridyl | 4-pyridyl | pale yellow crystals | 210–211 |
| 18 | 2-(4-Phenethyl-1-piperazinyl)-7-(4-pyridyl)-[1,2,4]triazolo[1,5-a]pyrimidine | 4-pyridyl | —CH₂CH₂—phenyl | pale yellow crystals | 178–180 |
| 19 | 2-(4-Methyl-1-piperazinyl)-7-(4-pyridyl)[1,2,4]triazolo[1,5-a]pyrimidine | 4-pyridyl | —CH₃ | pale yellow crystals | 203–204 |
| 20 | 2-(4-Furfuryl-1-piperazinyl)-7-(4-pyridyl)-[1,2,4]triazolo[1,5-a]pyrimidine | 4-pyridyl | —CH₂—furyl | yellow prisms | 188–190 |
| 21 | 2-(4-Cyclopenyl-1-piperazinyl)-7-(3-pyridyl)-[1,2,4]triazolo[1,5-a]pyrimidine | 3-pyridyl | cyclopentyl | pale yellow crystals | 170–172 |
| 22 | 2-(4-Cyclopentyl-1-piperazinyl)-7-(4-pyridyl)-[1,2,4]triazolo[1,5-a]pyrimidine | 4-pyridyl | cyclopentyl | pale yellow crystals | 187–188 |
| 23 | 4-[7-(4-Pyridyl)[1,2,4]triazolo[1,5-a]pyrimidin-2-yl]-1-piperazinecarboxaldehyde | 4-pyridyl | —CHO | yellow crystals | 220–232 |

TABLE II-continued
2-(4-Substituted-1-piperazinyl)-7-substituted[1,2,4]triazolo[1,5-a]pyrimidines

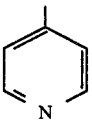

| Ex. | Compound | R₃ | R₄ | Description | MP °C. |
|---|---|---|---|---|---|
| 24 | 4-[7-(4-Pyridyl)[1,2,4]-triazolo[1,5-a]pyrimidin-2-yl]-1-piperazine carboxylic acid, benzyl ester | 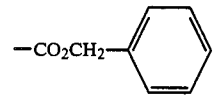 | —CO₂CH₂—  | yellow crystals | 173–175 |
| 25 | 7-Diphenylmethyl-2-(4-phenethyl-1-piperazinyl)-[1,2,4]triazolo[1,5-a]-pyrimidine | 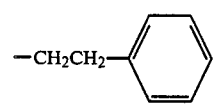 | —CH₂CH₂— 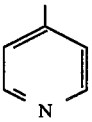 | off-white crystals | 155–156 |
| 26 | 2-[4-m-Chlorobenzyl-1-piperazinyl]-7-(4-pyridyl)[1,2,4]triazolo[1,5-a]-pyrimidine | 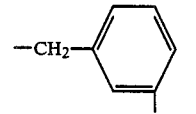 | —CH₂— 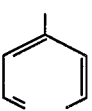 | yellow crystals | 165–167 |
| 27 | 2-[4-[(3,4-Dichlorophenyl-methyl]-1-piperazinyl]-7-(4-pyridyl)[1,2,4]tria-zolo[1,5-a]pyrimidine | 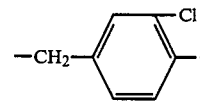 | —CH₂— 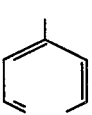 | yellow crystals | 184–186 |
| 28 | 2-[4-(2-Propenyl)-1-piperazinyl]-7-(4-pyri-dinyl([1,2,4]triazolo-[1,5-a]pyrimidine | 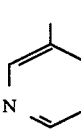 | CH₂CH=CH₂ | yellow crystals | 157–159 |
| 29 | 4-[7-(3-Pyridyl)[1,2,4]-triazolo[1,5-a]pyrimidin-2-yl]-1-piperazinecarbox-ylic acid, benzyl ester | 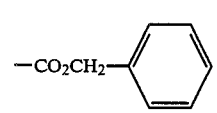 | —CO₂CH₂— 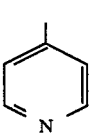 | colorless crystals | 136–138 |
| 30 | 2-[4-[2-(4-Bromophenoxy)-ethyl]-1-piperazinyl]-7-[4-pyridinyl][1,2,4]tria-zolo[1,5-a]pyrimidine | 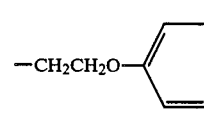 | —CH₂CH₂O—  —Br | yellow crystals | 163–165 |
| 31 | 7-(3-Chlorophenyl)-2-[4-[(3,4-dichlorophenyl)-methyl]-1-piperazinyl]-[1,2,4]triazolo[1,5-a]-pyrimidine | 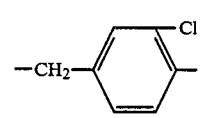 | —CH₂— 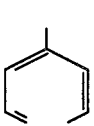 | yellow crystals | 256–257 |
| 32 | N—(1-Methylethyl)-4-[7-(4-pyridinyl)[1,2,4]triazolo-[1,5-a]pyrimidin-2-yl]-1-piperazineacetamide | 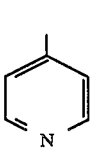 | —CH₂CONHCH(CH₃)₂ | pale yellow crystals | 171–174 |
| 33 | 2-[4-(3-Phenoxypropyl)-1-piperazinyl]-7-(4-pyri-dinyl)[1,2,4]triazolo-[1,5-a]pyrimidine | 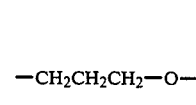 | —CH₂CH₂CH₂—O—  | yellow crystals | 96–98 |

TABLE II-continued 2-(4-Substituted-1-piperazinyl)-7-substituted[1,2,4]triazolo[1,5-a]pyrimidines

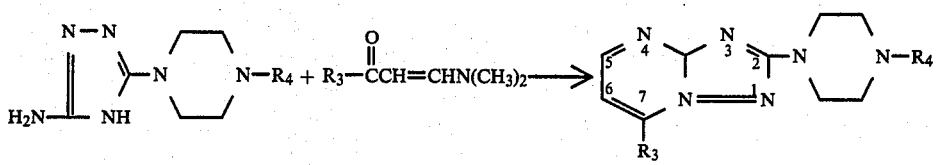

| Ex. | Compound | R₃ | R₄ | Description | MP °C. |
|---|---|---|---|---|---|
| 34 | 2-[4-(4-Phenoxybutyl)-1-piperazinyl]-7-(4-pyridinyl)[1,2,4]triazolo-[1,5-a]pyrimidine | 4-pyridinyl | —CH$_2$(CH$_2$)$_2$CH$_2$O—phenyl | pale yellow crystals | 126–127 |
| 35 | 2-[4-[(2-Phenyl-2H—1,2,3-triazol-4-yl)methyl]-1-piperazinyl]-7-(4-pyridinyl)[1,2,4]triazolo-[1,5-a]pyrimidine | 4-pyridinyl | —CH$_2$-(2-phenyl-2H-1,2,3-triazol-4-yl) | yellow crystals | 140–141 (dec.) |
| 36 | 2-[4-(2-Phenoxyethyl)-1-piperazinyl]-7-(4-pyridinyl)[1,2,4]triazolo-[1,5-a]pyrimidine | 4-pyridinyl | —CH$_2$CH$_2$—O—phenyl | yellow crystals | 150–152 |
| 37 | 2-[4-(3-Phenyl-2-propenyl)-1-piperazinyl]-7-(4-pyridinyl)[1,2,4]triazolo[1,5-a]pyrimidine | 4-pyridinyl | —CH$_2$CH=CH—phenyl | yellow solid | 162–163 |

EXAMPLE 38

4-(5,7-Dipropyl[1,2,4]triazolo[1,5-a]pyrimidin-2-yl)-1-piperazinecarboxylic acid, ethyl ester A mixture of 4.48 g (0.02 moles) of 4-(5-amino-4H-1,2,4-triazol-3-yl)-1-piperazinecarboxylic acid, ethyl ester, 3.12 g (0.02 moles) of 4,6-nonanedione and 50 ml of glacial acetic acid was refluxed for 12 hours. The resulting solution was evaporated to dryness in vacuo. The residue was partitioned and treated as described in Example 12 and gave 6.77 g of the desired product as colorless crystals, mp 130°–132° C.

EXAMPLES 39–42

Additional examples of 2-(4-substituted-1-piperazinyl)-5,7-substituted[1,2,4]triazolo[1,5-a]pyrimidines which are listed in Table III were prepared in the manner described in Example 38 by reacting equimolar amounts of a 1-(5-amino-4H-1,2,4-triazol-3-yl)-4-substituted piperazine (hereinabove disclosed or prepared as described in U.S. Pat. No. 4,421,753) and a dione such as 4,6-nonanedione or 4,4,4-trifluoro-1-(4-pyridyl)-1,3-butanedione. Acid addition salts were obtained by treating the free base compound with 2N hydrochloric acid with or without the aid of diethyl ether.

TABLE III 2-(4-Substituted-1-piperazinyl)-5,7-substituted[1,2,4]triazolo[1,5-a]pyrimidines

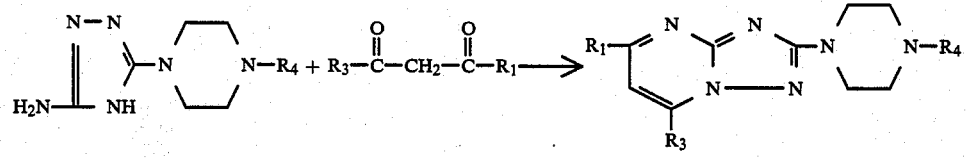

| Ex. | Compound | R₁ | R₃ | R₄ | Description | MP °C. |
|---|---|---|---|---|---|---|
| 39 | 2-(4-Benzyl-1-piperazinyl)-5,7-dipropyl[1,2,4]triazolo[1,5-a]pyrimidine | C$_3$H$_7$—n | C$_3$H$_7$—n | —CH$_2$—phenyl | colorless crystals | 52–54 |

TABLE III-continued 2-(4-Substituted-1-piperazinyl)-5,7-substituted[1,2,4]triazolo[1,5-a]pyrimidines

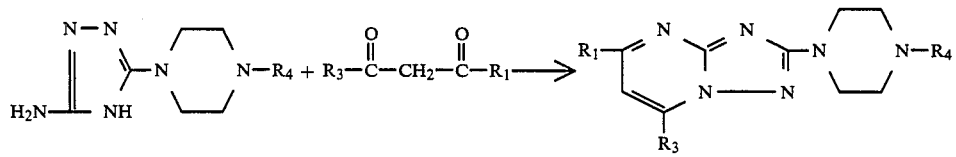

| Ex. | Compound | $R_1$ | $R_3$ | $R_4$ | Description | MP °C. |
|---|---|---|---|---|---|---|
| 40 | 2-[4-[(3-Chlorophenyl)-methyl]-1-piperazinyl]-5,7-dipropyl[1,2,4]triazolo[1,5-a]pyrimidine, monohydrochloride | $C_3H_7$—n | $C_3H_7$—n | —CH₂—(3-chlorophenyl) | colorless crystals | 245–247 (dec.) |
| 41 | 2-[4-(4-Phenoxybutyl)-1-piperazinyl[-5,7-dipropyl[1,2,4]triazolo[1,5-a]-pyrimidine, monohydrochloride | $C_3H_7$—n | $C_3H_7$—n | —CH₂(CH₂)₂CH₂O—phenyl | colorless crystals | 143–145 |
| 42 | 2-[4-(Phenylmethyl)-1-piperazinyl]-7-(pyridinyl)-5-(trifluoromethyl)[1,2,4]triazolo-[1,5-a]pyrimidine | —CF₃ | 4-pyridinyl | —CH₂—phenyl | yellow solid | 216–218 |

EXAMPLE 43

6-Bromo-2-[4-(4-phenoxybutyl)-1-piperazinyl][1,2,4]-triazolo[1,5-a]pyrimidine

A 10.0 g (0.03 mole) amount of 5-[4-(4-phenoxybutyl)-1-piperazinyl]-4H-1,2,4-triazol-3-amine, dihydrochloride was partially dissolved in 20 ml of water, then 5N sodium hydroxide was added to adjust the pH to just greater than pH 7, resulting in formation of a solid. The solid was collected by filtration and washed with water. The colorless crystals, were transfered into a 125 ml round bottom flask and dissolved in 50 ml of ethanol. Then 7.5 g (0.05 moles) of bromomalonaldehyde was added and the mixture was heated at reflux for 7 hours. The reaction mixture was cooled and filtered. The filter was washed with ethanol/ether, then ether. The filtrate was evaporated in vacuo, combined with the filter cake, extracted with hot chloroform and filtered. The filtrate was passed through a pad of magnesium silicate and the pad was washed with chloroform. The combined chloroform filtrate and wash was evaporated to a syrup. Crystallization from ethanol gave 2.2 g of the desired product as pale yellow crystals, mp 122°–123° C.

EXAMPLES 44–46

Additional examples of 2-(4-substituted-1-piperazinyl)-6-bromo[1,2,4]triazolo[1,5-a]pyrimidines which are listed in Table IV were prepared in the manner described in Example 43 by refluxing a 1-(5-amino-4H-1,2,4-triazol-3-yl)-4-substituted piperazine (hereinabove disclosed or prepared as described in U.S. Pat. No. 4,421,753) with slight excess of a malonaldehyde such as bromomalonaldehyde in ethanol for 4–18 hours and recrystallizing the product from a solvent such as ethanol, methanol or acetone.

TABLE IV 2-(4-Substituted-1-piperazinyl)-6-bromo[1,2,4]triazolo[1,5-a]pyrimidines

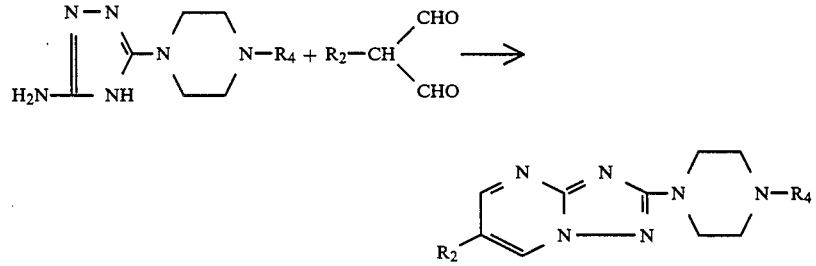

| Ex. | Compound | $R_2$ | $R_4$ | Description | MP °C. |
|---|---|---|---|---|---|
| 44 | 4-(6-Bromo[1,2,4]triazolo-[1,5-a]pyrimidin-2-yl-N—(1-methylethyl)-1-piperazineacetamide | Br | —CH₂CONHCH(CH₃)₂ | cream colored solid | 156–157 |

TABLE IV-continued
2-(4-Substituted-1-piperazinyl)-6-bromo[1,2,4]triazolo[1,5-a]pyrimidines

| Ex. | Compound | R$_2$ | R$_4$ | Description | MP °C. |
|---|---|---|---|---|---|
| 45 | 6-Bromo-2-[4-[2-(4-bromo-phenoxy)ethyl]-1-piperazinyl][1,2,4]triazolo-[1,5-a]pyrimidine | Br | —CH$_2$CH$_2$O—C$_6$H$_4$—Br | cream colored crystals | 164–165 |
| 46 | 6-Bromo-2-[4-(phenyl-methyl)-1-piperazinyl]-[1,2,4]triazolo[1,5-a]-pyrimidine | Br | —CH$_2$—C$_6$H$_5$ | beige crystals | 151–152 |

EXAMPLE 47
2-(1-Piperazinyl)-7-(4-pyridyl)[1,2,4]triazolo-[1,5-a]pyrimidine

To an 8.0 g amount of 4-[7-(4-pyridyl)[1,2,4]-triazolo[1,5-a]pyrimidin-2-yl]-1-piperazine carboxylic acid benzyl ester in 125 ml round bottom flask was added 25.0 ml of hydrobromic acid (31% in glacial acetic acid). The mixture was allowed to react for 20 minutes then was cooled. Ether was added to separate the precipitate. The precipitate was collected by filtration and dissolved in water. The solution was adjusted to a pH greater than pH 7 with 5N sodium hydroxide and extracted with three equal portions of chloroform. The extracts were combined and evaporated in vacuo to a syrup. The syrup was dissolved in hot ethanol and hexane was added to crystallize the crude product which was collected and washed with hexane. The crude product was recrystallized from 25 ml of cold ethanol, filtered, washed with ethanol/hexane then hexane. The material was dried in vacuo at 60° C. and gave 4.2 g of the product of the example as yellow crystals, mp 147°–149° C.

EXAMPLE 48
2-(1-Piperazinyl)-7-(3-pyridinyl)[1,2,4]triazolo-[1,5-a]pyrimidine To a 2.5 g amount of 4-[7-(3-pyridyl)[1,2,4]-triazolo[1,5-a]pyrimidin-2-yl]-1-piperazinecarboxylic acid benzyl ester was added 5.0 ml of hydrobromic acid (31% in glacial acetic acid). The mixture was allowed to react for 4 hours then was cooled to room temperature. Anhydrous ether was added, the mixture was swirled and the liquid decanted. This step was repeated several times. The residual precipitate was dissolved in water and the solution was filtered. The filtrate was made basic with 5N sodium hydroxide and extracted several times with dichloromethane. The extracts were combined and heated to boiling, then hexane was added to crystallize the product. Cooling and filtration gave 1.10 g of the deseired product as pale yellow crystals, mp 156°–158° C.

EXAMPLE 49
1-Phenyl-2-[4-[7-(4-pyridinyl)[1,2,4]triazolo-[1,5-a]pyrimidin-2-yl]-1-piperazinyl]-1-propanone A mixture of 5.6 g (0.02 moles) of 2-(1-piperazinyl)-7-(4-pyridyl)[1,2,4]triazolo[1,5-a]pyrimidine (prepared as described in Example 47) and 4.2 g (0.02 moles) of α-bromopropiophenone in 100 ml of 2-propanol containing 3.6 ml (0.026 moles) of triethylamine was heated at the reflux temperature for 24 hours. The reaction mixture was evaporated to dryness in vacuo. Then 100 ml of water was added to the residue and the mixture was extracted three times with a total of 100 ml of chloroform. The combined extracts were dried over magnesium sulfate and filtered. The filtrate was passed through a pad of magnesium silicate, washing with chloroform. The filtrate was evaporated to a syrup. The syrup was dissolved in 20 ml of ethanol and 200 ml of diethyl ether was added, then hexane was added until cloudy. The mixture was evaporated by boiling to about 100 ml, then was cooled and filtered to collect the precipitate, which was washed with ether and gave 2.3 g of the desired product as yellow crystals, mp 142°–144° C.

EXAMPLE 50
4-[7-(4-Pyridinyl)[1,2,4]triazolo[1,5-a]pyrimidin-2-yl]-1-piperazinebutanenitrile A mixture of 5.6 g (0.02 moles) of 2-(1-piperazinyl)-7-(4-pyridyl)[1,2,4]triazolo[1,5-a]pyrimidine (prepared as described in Example 47), 3.0 g (0.02 moles) of 4-bromobutyronitrile, 4.0 g of potassium carbonate and 50 ml of N,N-dimethylformamide was heated at reflux for 16 hours with stirring. The mixture was cooled and filtered. The filter was washed with N,N-dimethylformamide and the combined filtrate and wash was evaporated in vacuo to give a dark syrup. The syrup was dissolved in chloroform and passed through a pad of magnesium silicate washing with chloroform. The filtrate was evaporated to a syrup and crystallized from ethanol/ether. The precipitate was collected by filtration and washed with ether and gave 2.1 g of the desired product as golden crystals, mp 147°–148° C.

EXAMPLE 51

1-(4-Fluorophenyl)-4-[4-[7-(4-pyridinyl)[1,2,4]triazolo-[1,5-a]pyrimidin-2-yl]-1-piperazinyl]-1-butanone A mixture of 5.6 g (0.02 moles) of 2-(1-piperazinyl)-7-(4-pyridyl)[1,2,4]triazolo[1,5-a]pyrimidine (prepared as described in Example 47), 4.0 g (0.02 moles) of α-chloro-p-fluorobutyrophenone, 3.6 g (0.027 moles) of N,N-diisopropylethylamine and 100 ml of 2-propanol was heated at reflux for 16 hours with stirring. The reaction mixture was evaporated in vacuo to a solid. The solid was dissolved in 100 ml of water and extracted twice with 100 ml of chloroform. The extracts were combined, dried over magnesium sulfate, filtered and evaporated to a dark syrup. The syrup was dissolved in dichloromethane and passed through a pad of magnesium silicate, washing with methylene chloride. This filtrate was collected and set aside. Then acetone was passed through the pad and the acetone filtrate was collected and evaporated to a syrup. The syrup was dissolved in 15 ml of ethanol, 200 ml of ether was added, then hexane until cloudy. Evaporation by boiling caused crystallization. The crude product was collected and washed with ether. Recrystallization from ethanol gave 1.2 g of the desired product as yellow crystals, mp 133°–135° C.

EXAMPLE 52

α-(Phenoxymethyl)-4-[7-(4-pyridinyl)[1,2,4]triazolo-[1,5-a]pyrimidin-2-yl]-1-piperazineethanol A mixture of 2.6 g (0.0093 moles) of 2-(1-piperazinyl)-7-(4-pyridyl)[1,2,4]triazolo[1,5-a]pyrimidine (prepared as described in Example 47), 1.4 g (0.0093 moles) of 2,3-epoxypropoxybenzene and 25.0 ml of 2-propanol was heated at reflux for 5 hours. The reaction mixture was evaporated in vacuo and gave a solid. The solid was dissolved in dichloromethane and passed through a pad of magnesium silicate. The effluent was evaporated to a solid. The solid was recrystallized from ethanol/ether/hexane, filtered, and washed with ether and gave 600 mg of the product of the Example as yellow crystals, mp 143°–145° C.

EXAMPLE 53

7-(5-Methyl-2-phenyl-1H-imidazol-4-yl)-2-[4-phenylmethyl)-1-piperazinyl][1,2,4]triazolo[1,5-a]pyrimidine A mixture of 10.0 g (0.05 moles) of methyl 5-methyl-2-phenyl-4-imidazolyl ketone [A. C. Verones, et al., J. Het. Chem., 17, 1723 (1980)] and 45.0 ml of N,N-dimethylformamide dimethyl acetal was refluxed for 16 hours in an oil bath. The reaction mixture was cooled at −10° C., then filtered. The product was washed with 50 ml of cold ethanol, air dried and gave 4.6 g of 3-(dimethylamino)-1-(5-methyl-2-phenyl-1H-imidazol-4-yl)-2-propen-1-one as a yellow solid, mp 218°–222° C.

A mixture of 2.2 g (0.009 moles) of the preceding product, 2.2 g of 1-(5-amino-4H-1,2,4-triazol-3-yl)-4-benzylpiperazine and 100 ml of glacial acetic acid was refluxed for 8 hours. The reaction mixture was evaporated to dryness in vacuo and gave an oil. The oil was slurried in 100 ml of saturated sodium bicarbonate and gave a tacky precipitate. The mixture was extracted three times with a total of 250 ml of dichloromethane. The combined extracts were dried over magnesium sulfate then filtered through a pad of magnesium silicate and washed with 200 ml of chloroform. The filtrate and wash were combined and evaporated to dryness in vacuo. The residue was triturated with 100 ml of hexane. The solid was collected by filtration and washed with hexane and gave 1.9 g of the desired product as a yellow solid, mp 100°–103° C.

EXAMPLE 54

N'-[[2-Chloro-5-[2-[4-(phenylmethyl)-1-piperazinyl]-[1,2,4]-triazolo[1,5-a]pyrimidin-7-yl]phenyl]sulfonyl]-N-N-dimethylmethanimidamide A mixture of 7.8 g (0.033 moles) of 5-acetyl 2-chlorobenzenesulfonamide [Chem. Abst., 63, 5563a (1965)] and 50 ml of N,N-dimethylformamide dimethyl acetal was refluxed for 5 hours, then cooled at −10° C. The precipitate formed was collected, washed with 50 ml of ether and air dried. The solid was boiled up in 400 ml of ethanol, treated with activated charcoal and filtered. The filtrate was cooled at −10° C. and filtered to collect an orange-red precipitate. The solid was washed with 50 ml of ethanol and dried in vacuo at 60° C. and gave 5.2 g of N'-[[2-chloro-5-[3-(dimethylamino)-1-oxo-2-propenyl]-phenyl]sulfonyl]-N,N-dimethylmethanimidamide, mp 204°–206° C.

A mixture of 3.43 g (0.01 mole) of the preceding product and 2.58 g (0.01 mole) of 1-(5-amino-4H-1,2,4-triazol-3-yl)-4-benzylpiperazine (prepared as described in Example 10) in 100 ml of glacial acetic acid was heated on a steam bath for ten hours. Then the solution was heated at the reflux temperature for 2 hours. The solution was taken to dryness in vacuo. The residue was treated with 100 ml of saturated sodium bicarbonate to separate a solid. The mixture was extracted with 250 ml of dichloromethane. The organic layer was dried over magnesium sulfate and filtered. The filtrate was passed through diatomaceous earth. The filter was washed with 700 ml of dichloromethane. The combined filtrate and wash was evaporated in vacuo and gave a yellow precipitate. The precipitate was slurried in 100 ml of hexane, filtered, washed with hexane, air dried, then dried in vacuo at 60° C. and gave 1.9 g of the product of the Example as a yellow solid, mp 120°–122° C.

We claim:

1. A compound selected from the group consisting of those of the formula:

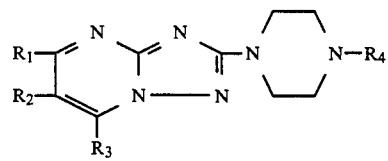

wherein R$_1$ is hydrogen, n-propyl or trifluoromethyl; R$_2$ is hydrogen or bromo; R$_3$ is selected from the group consisting of hydrogen, n-propyl, 3-chlorophenyl, 2,5-dichlorophenyl, 3-trifluoromethylphenyl, 2-furyl, 3-pyridyl, 4-pyridyl, diphenylmethyl and moieties of the formulae:

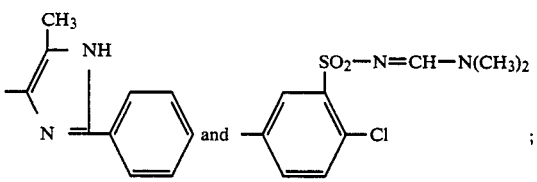

and R4 is selected from the group consisting of hydrogen, methyl, formyl, carboethoxy, carbobenzyloxy, benzyl, 3-chlorobenzyl, 3,4-dichlorobenzyl, β-phenethyl, furfuryl, 4-pyridyl, cyclopentyl, N-isopropylaminocarbonylmethyl, 3-cyanopropyl, 3-(4-fluorobenzoyl)propyl, 2-propenyl, 2-benzoylethyl, 3-phenyl-2-propenyl, 2-phenoxyethyl, 3-phenoxypropyl, 4-phenoxybutyl, 2-(4-bromophenoxy)ethyl, 2-hydroxy-3-phenoxypropyl and a moiety of the formula:

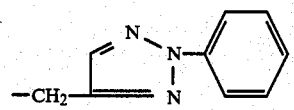

and the pharmacologically acceptable acid-addition salts thereof.

2. The compound in accordance with claim 1; 2-(4-benzyl-1-piperazinyl)-7-(4-pyridyl)[1,2,4]triazolo[1,5-a]pyrimidine.

3. The compound in accordance with claim 1; 7-(4-pyridyl)-2-[4-(4-pyridylmethyl)-1-piperazinyl][1,2,4]-triazolo[1,5-a]pyrimidine.

4. The compound in accordance with claim 1; 4-(5,7-dipropyl[1,2,4]triazolo[1,5-a]pyrimidin-2-yl)-1-piperazinecarboxylic acid, ethyl ester.

5. The compound in accordance with claim 1; 2-(4-phenethyl-1-piperazinyl)-7-(4-pyridyl)[1,2,4]-triazolo[1,5-a]pyrimidine.

6. The compound in accordance with claim 1; 7-diphenylmethyl-2-(4-phenethyl-1-piperazinyl)[1,2,4]-triazolo[1,5-a]pyrimidine.

7. The compound in accordance with claim 1; 2-(4-cyclopentyl-1-piperazinyl)-7-(3-pyridyl)[1,2,4]-triazolo[1,5-a]pyrimidine.

8. The compound in accordance with claim 1; 2-(1-piperazinyl)-7-(4-pyridyl)[1,2,4]triazolo[1,5-a]-pyrimidine.

9. The compound in accordance with claim 1; 2-(1-piperazinyl)-7-(3-pyridyl)[1,2,4]triazolo[1,5-a]-pyrimidine.

10. The compound in accordance with claim 1; N-(1-methylethyl)-4-[7-(4-pyridyl)[1,2,4]triazolo[1,5-a]-pyrimidin-2-yl]-1-piperazineacetamide.

11. The compound in accordance with claim 1; 4-[7-(4-pyridyl)[1,2,4]triazolo[1,5-a]pyrimidin-2-yl]-1-piperazinebutanenitrile.

12. The compound in accordance with claim 1; 1-(4-fluorophenyl)-4-[4-[7-(4-pyridyl)[1,2,4]-triazolo-[1,5-a]pyrimidin-2-yl]-1-piperazinyl]-1-butanone.

13. The compound in accordance with claim 1; 2-[4-[(2-phenyl-2H-1,2,3-triazol-4-yl)methyl]-1-piperazinyl]-7-(4-pyridyl)[1,2,4]triazolo[1,5-a]pyrimidine.

14. The compound in accordance with claim 1; 2-[4-(phenylmethyl)-1-piperazinyl]-7-(4-pyridyl)-5-(trifluoromethyl)[1,2,4]triazolo[1,5-a]pyrimidine.

15. The compound in accordance with claim 1; 2-[4-(2-phenoxyethyl)-1-piperazinyl]-7-(4-pyridyl)[1,2,4]-triazolo[1,5-a]pyrimidine.

16. The compound in accordance with claim 1; 2-[4-(4-phenoxybutyl)-1-piperazinyl]-5,7-dipropyl[1,2,4]-triazolo[1,5-a]pyrimidine, monohydrochloride.

17. The compound in accordance with claim 1; 2-[4-(3-phenoxypropyl)-1-piperazinyl]-7-(4-pyridyl)-[1,2,4]triazolo[1,5-a]pyrimidine.

18. A method of treating hypertension in a warm-blooded animal which comprises administering to said animal an effective amount of a compound of claim 1.

19. A hypotensive composition of matter in dosage unit form comprising from about 50 mg to about 250 mg per dosage unit of a compound of claim 1 in association with a pharmaceutical carrier.

* * * * *